United States Patent [19]
Chang

[11] Patent Number: 5,885,820
[45] Date of Patent: Mar. 23, 1999

[54] CLONE OF A NUCLEOTIDE SEQUENCE ENCODING A PROTEIN HAVING TWO FUNCTIONS

[75] Inventor: Yie-Hwa Chang, St. Louis, Mo.

[73] Assignee: St. Louis University, St. Louis, Mo.

[21] Appl. No.: 40,799

[22] Filed: Mar. 18, 1998

Related U.S. Application Data

[63] Continuation of Ser. No. 595,025, Jan. 31, 1996.

[51] Int. Cl.$^6$ .............................. C12N 9/48; C12N 15/00; C12N 1/20; C07H 21/04
[52] U.S. Cl. ................ 435/212; 435/252.3; 435/254.11; 435/320.1; 435/325; 435/348; 536/23.2; 935/22
[58] Field of Search ................................ 435/212, 320.1, 435/325, 252.3, 254.11, 348; 536/23.2; 935/22

[56] References Cited

U.S. PATENT DOCUMENTS

| | | | |
|---|---|---|---|
| 4,865,974 | 9/1989 | Ben-Bassat et al. | 435/68 |
| 5,322,774 | 6/1994 | Peakman et al. | 435/69.1 |
| 5,470,719 | 11/1995 | Meng et al. | 435/69.1 |
| 5,608,036 | 3/1997 | Meng et al. | 530/324 |
| 5,618,685 | 4/1997 | Darke et al. | 435/23 |

OTHER PUBLICATIONS

Arfin et al., Eukaryotic methionyl aminopeptidases: Two classes of cobalt–dependant enzymes, *Proc. Natl. Acad. Sci. USA* 92:7714–7718 (1995).
Li et al., Molecular cloning of a human complementary DNA encoding an initiation factor 2–associated protein (p.$^{67}$)*, *Biochimica et Biophysica Acta 1260*:3330336 (Feb. 21, 1995).
Arfin et al., Cotranslational processing and protein turnover in eukaryotic cells, *Biochemistry* 27(21):7979–7984.
Ball et al., *J. Mol. Biol.* 79:531–537 (1973).
Bazan et al., Sequence and structure comparison suggest that methionone aminopeptidase, prolidase, aminopeptidase P, and creatinase share a common fold, *Proc. of the Natl. Acad. of Sci. USA* 91:2473–2477 (1994).
Ben–Bassat et al., *J. Bacteriol.* 169:751–757 (1987).
Chang et al., *J. Biol. Chem.* 265:19892–19897 (1990).
Chang et al., *J. Biol. Chem.* 267:8007–8011 (1992).
Duronio et al., *Science* 243:796–800 (1989).
Gordon et al., *J. Biol. Chem.* 266:8647–8650 (1991).
Huang et al., *Biochemistry* 26:8242–8246 (1987).
Kendall et al., *J. Biol. Chem.* 267:20667–20673 (1992).
Kozak, *J. Biol. Chem.* 26:19867–19870 (1991).
Li et al., *Proc. Natl. Acad. Sci USA* 92:12375–12361 (1995).
Meinnel et al., Methionine as translation start signal: A review of the enzymes of the pathway in *Escherichia coli*, *Biochimie* 75:1061–1075.
Miller et al., *Proc. Natl. Acad. Sci. USA* 84:2718–2722 (1987).
Moerschell et al., *J. Biol. Chem.* 265:19638–19643 (1990).
Ngo et al., Computational complexity, protein structure prediction, and the Levinthal paradox. In: The Protein Folding Problem and Tertiary Structure Prediction, *Eds. Merz et al.*, Birkhauser, Boston, MA 491–495 (1994).
Ray et al., *Biochemistry* 32:5151–5159 (1993).
Roderick et al., *Biochemistry* 32:3907–3912 (1993).
Wu et al., Cloning and characterization of complementary DNA encoding the eukaryotic initiation factor 2–associated 67–kDa protein (p.67), *J. Bio. Chem.* 268(15):10796–10801 (1993).

*Primary Examiner*—Karen Cochrane Carlson
*Assistant Examiner*—Einar Stole
*Attorney, Agent, or Firm*—Howell & Haferkamp, L.C.

[57] ABSTRACT

A nucleotide sequence which encodes a protein which is substantially similar to eukaryotic initiation factor-2 (eIF-2) associated glycoprotein (p67) and also has methionine amino peptidase activity. The encoded protein may facilitate protein synthesis by protecting eIF-2 from phosphorylation and prepare the protein for critical cellular role by removing N-terminal methionine.

16 Claims, 3 Drawing Sheets

```
 -34                                       ctctgtctcattccctcgcgctctctcgggcaac
   1 ATGGCGGGTGTGGAGGAGGTAGCGGCCTCCGGGAGCCACCTGAATGGCGACCTGGATCCA
     M   A   G   V   E   E   V   A   A   S   G   S   H   L   N   G   D   L   D   P    20
  61 GACGACAGGGAAGAAGGAGCTGCCTCTACGGCTGAGGAAGCAGCCAAGAAAAAAGACGA
     D   D   R   E   E   G   A   A   S   T   A   E   E   A   A   K   K   K   R   R    40
 121 AAGAAGAAGAAGAGCAAAGGGCCTTCTGCAGCAGGGGAACAGGAACCTGATAAAGAATCA
     K   K   K   K   S   K   G   P   S   A   A   G   E   Q   E   P   D   K   E   S    60
 181 GGAGCCTCAGTGGATGAAGTAGCAAGACAGTTGGAAAGATCAGCATTGGAAGATAAAGAA
     G   A   S   V   D   E   V   A   R   Q   L   E   R   S   A   L   E   D   K   E    80
 241 AGAGATGAAGATGATGAAGATGGAGATGGCGATGGAGATGGAGCAACTGGAAAGAAGAAG
     R   D   E   D   D   E   D   G   D   G   D   G   D   G   A   T   G   K   K   K   100
 301 AAAAAGAAGAAGAAGAAGAGAGGACCAAAAGTTCAAACAGACCCTCCCTCAGTTCCAATA
     K   K   K   K   K   R   G   P   K   V   Q   T   D   P   P   S   V   P   I       120
 361 TGTGACCTGTATCCTAATGGTGTATTTCCCAAAGGACAAGAATGCGAATACCCACCCACA
     C   D   L   Y   P   N   G   V   F   P   K   G   Q   E   C   E   Y   P   P   T   140
 421 CAAGATGGGCGAACAGCTGCTTGGAGAACTACAAGTGAAGAAAAGAAAGCATTAGATCAG
     Q   D   G   R   T   A   A   W   R   T   T   S   E   E   K   K   A   L   D   Q   160
 481 GCAAGTGAAGAGATTTGGAATGATTTTCGAGAAGCTGCAGAAGCACATCGACAAGTTAGA
     A   S   E   E   I   W   N   D   F   R   E   A   A   E   A   H   R   Q   V   R   180
 541 AAATACGTAATGAGCTGGATCAAGCCTGGGATGACAATGATAGAAATCTGTGAAAAGTTG
     K   Y   V   M   S   W   I   K   P   G   M   T   M   I   E   I   C   E   K   L   200
 601 GAAGACTGTTCACGCAAGTTAATAAAAGAGAATGGATTAAATGCAGGCCTGGCATTTCCT
     E   D   C   S   R   K   L   I   K   E   N   G   L   N   A   G   L   A   F   P   220
 661 ACTGGATGTTCTCTCAATAATTGTGCTGCCCATTATACTCCCAATGCCGGTGACACAACA
     T   G   C   S   L   N   N   C   A   A   H   Y   T   P   N   A   G   D   T   T   240
 721 GTATTACAGTATGATGACATCTGTAAAATAGACTTTGGAACACATATAAGTGGTAGGATT
     V   L   Q   Y   D   D   I   C   K   I   D   F   G   T   H   I   S   G   R   I   260
 781 ATTGACTGTGCTTTTACTGTCACTTTTAATCCCAAATATGATACGTTATTAAAAGCTGTA
     I   D   C   A   F   T   V   T   F   N   P   K   Y   D   T   L   L   K   A   V   280
 841 AAAGATGCTACTAACACTGGAATAAAGTGTGCTGGAATTGATGTTCGTCTGTGTGATGTT
     K   D   A   T   N   T   G   I   K   C   A   G   I   D   V   R   L   C   D   V   300
 901 GGTGAGGCCATCCAAGAAGTTATGGAGTCCTATGAAGTTGAAATAGATGGGAAGACATAT
     G   E   A   I   Q   E   V   M   E   S   Y   E   V   E   I   D   G   K   T   Y   320
 961 CAAGTGAAACCAATCCGTAATCTAAATGGACATTCAATTGGGCAATATAGAATACATGCT
     Q   V   K   P   I   R   N   L   N   G   H   S   I   G   Q   Y   R   I   H   A   340
1021 GGAAAAACAGTGCCGATTGTGAAAGGAGGGGAGGCAACAAGAATGGAGGAAGGAGAAGTA
     G   K   T   V   P   I   V   K   G   G   E   A   T   R   M   E   E   G   E   V   360
1081 TATGCAATTGAAACCTTTGGTAGTACAGGAAAAGGTGTTGTTCATGATGATATGGAATGT
     Y   A   I   E   T   F   G   S   T   G   K   G   V   V   H   D   D   M   E   C   380
1141 TCACATTACATGAAAAATTTTGATGTTGGACATGTGCCAATAAGGCTTCCAAGAACAAAA
     S   H   Y   M   K   N   F   D   V   G   H   V   P   I   R   L   P   R   T   K   400
1201 CACTTGTTAAATGTCATCAATGAAAACTTTGGAACCCTTGCCTTCTGCCGCAGATGGCTG
     H   L   L   N   V   I   N   E   N   F   G   T   L   A   F   C   R   R   W   L   420
1261 GATCGCTTGGGAGAAAGTAAATACTTGATGGCTCTGAAGAATCTGTGTGACTTGGGCATT
     D   R   L   G   E   S   K   Y   L   M   A   L   K   N   L   C   D   L   G   I   440
1321 GTAGATCCATATCCACCATTATGTGACATTAAAGGATCATATACAGCGCAATTTGAACAT
     V   D   P   Y   P   P   L   C   D   I   K   G   S   Y   T   A   Q   F   E   H   460
1381 ACCATCCTGTTGCGTCCAACATGTAAAGAAGTTGTCAGCAGAGGAGATGACTATtaaact
     T   I   L   L   R   P   T   C   K   E   V   V   S   R   G   D   D   Y           478
1441 tagtccaaagccacctcaacaccttattttctgagctttgttggaaaacatgataccag
1501 aattaatttgccacatgttgtctgttttaacagtggacccatgtaatacttttatccatg
1561 tttaaaaagaaggaatttggacaaaggcaaaccgtctaatgtaattaaccaacgaaaaag
1621 ctttccggacttttaaatgctaactgttttttcccttcctgtctaggaaatgctataaa
1681 gctcaaattagttaggaatgacttatacgttttgttttgaatacctaagagatacttttt
1741 ggatatttatattgccatattcttacttgaatgctttgaatgactacatccagttctgca
1801 cctatacctctggtgttgcttttaaccttcctggaatccatttctaaaaaataaagac
1861 attttcagatctgaaaaaaaaaaaaaaaaaaaa
```

Fig. 1

```
Rat:    1 MAGVEEASSFGGHLNRDLDPDDREEGTSSTAEEAAKKKRRKKKKGKGAVS
          |||||...  |:|||  ||||||||||..|||||||||||||||:||: .
Human:  1 MAGVEEVAASGSHLNGDLDPDDREEGAASTAEEAAKKKRRKKKKSKGPSA 51 AGQQELDKESGTSVDEVAKQLERQALEEKEKDDDDEDGDGDGDGAAGKKK
          ||:||  |||||.||||||:||||   |||:||:|:|||||||||||.||||
       51 AGEQEPDKESGASVDEVARQLERSALEDKERDEDDEDGDGDGDGATGKKK 101 KKKKKKRGPRVQTDPPSVPICDLYPNGVFPKGQECEYPPTQDGRTAAWRT
          ||||||||:|||||||||||||||||||||||||||||||||||||||||
      101 KKKKKKRGPKVQTDPPSVPICDLYPNGVFPKGQECEYPPTQDGRTAAWRT 151 TSEEKKALDQASEEIWNDFREAAEAHRQVRKYVMSWIKPGMTMIEICEKL
          ||||||||||||||||||||||||||||||||||||||||||||||||||
      151 TSEEKKALDQASEEIWNDFREAAEAHRQVRKYVMSWIKPGMTMIEICEKL 201 EDCSRKLIKENGLNAGLAFPTGCSLNNCAAHYTPNAGDTTVLQYDDICKI
          ||||||||||||||||||||||||||||||||||||||||||||||||||
      201 EDCSRKLIKENGLNAGLAFPTGCSLNNCAAHYTPNAGDTTVLQYDDICKI 251 DFGTHISGRIIDCAFTVTFNPKYDILLKAVKDATNTGIKCAGIDVRLCDV
          |||||||||||||||||||||||||.||||||||||||||||||||||||
      251 DFGTHISGRIIDCAFTVTFNPKYDTLLKAVKDATNTGIKCAGIDVRLCDV 301 GEAIQEVMESYEVEIDGKTYQVKPIRNLNGHSIGPYRIHAGKTVPIVKGG
          |||||||||||||||||||||||||||||||||.||||||||||||||||
      301 GEAIQEVMESYEVEIDGKTYQVKPIRNLNGHSIGQYRIHAGKTVPIVKGG 351 EATRMEEGEVYAIETFGSTGKGVVHDDMECSHYMKNFDVGHVPIRLPRTK
          ||||||||||||||||||||||||||||||||||||||||||||||||||
      351 EATRMEEGEVYAIETFGSTGKGVVHDDMECSHYMKNFDVGHVPIRLPRTK 401 HLLNVINENFGTLAFCRRWLDRLGESKYLMALKNLCDLGIVDPYPPLCDI
          ||||||||||||||||||||||||||||||||||||||||||||||||||
      401 HLLNVINENFGTLAFCRRWLDRLGESKYLMALKNLCDLGIVDPYPPLCDI 451 KGSYTAQFEHTILCAQPVKKLSAEEMTIKT  480
          ||||||||||||   ...|.:  . :
      451 KGSYTAQFEHTILLRPTCKEVVSRGDDY    478
```

Fig. 2

CLONE OF A NUCLEOTIDE SEQUENCE ENCODING A PROTEIN HAVING TWO FUNCTIONS

This application is a continuation of Ser. No. 08/595,025 filed Jan. 31, 1996.

HISTORY OF THE INVENTION

In all living cells, protein synthesis is initiated with an AUG codon. This initiation AUG codon specifies methionine in the cytosol of eukaryotes (1, 2). Eukaryotic initiation factor-2 plays a major role in this initiation event. The $NH_2$-methionine, in both eukaryotes and prokaryotes, will be removed by methionine aminopeptidases (MAPs), if the penultimate residue is small and uncharged, e.g. Ala, Cys, Gly, Pro, Ser, Thr and Val (2–5). Removal of the $NH_2$-methionine is essential for certain proteins to function normally in vivo. These proteins can be categorized into at least two groups. For the first group, the removal of the initiator methionine is required for subsequent N-terminal modifications, such as N-myristoylation, which is essential for their normal function, including signal transduction, certain cancer cell growth and protein targeting (6, 7). For the second group, the removal of the initiator methionine is required to allow the other N-terminal residues to function normally in their critical roles in catalysis. Some proteins when overexpressed in bacteria or other organisms, in which limited MAPs are available, may still have the undesired initiator methionine attached to their N-termini, and thus become nonfunctional. This problem may be reduced to certain extent by overexpressing the MAP together with the recombinant protein.

Eukaryotic MAPs have been purified and characterized from S. cerevisiae and porcine liver 8, 9). All bacterial and eukaryotic MAPs known to date are cobalt-dependent metallopeptidases, and they share similar substrate specificity. Favorable peptide substrates for MAPs possess an $NH_2$-terminal methionine followed by a small and uncharged residue, which is in general agreement with the specificities of MAPs predicted by the in vivo studies. Moreover, the X-ray structure of E. coli MAP was recently determined to 2.4 Å resolution (10). This bacterial MAP contains two cobalt ions in the active site and it appears to represent a new class of proteolytic enzymes. The genes encoding MAPs from E. coli, S. typhimurium and S. cerevisiae have been cloned and sequenced (3, 5, 11, 12).

Eukaryotic initiation factor-2 (eIF-2) comprises three subunits: α, β and γ. In mammals, there are several eIF-2 kinases, such as double-stranded RNA-activated inhibitor (dsI) and heme regulated inhibitor, which can specifically phosphorylate the alpha-subunit of eIF-2 under certain physiological conditions. Phosphorylation of eIF-2 alpha-subunit inactivates the function of eIF-2 and thereby inhibits protein synthesis. This regulatory mechanism is widely used in animal cells under nutritional deprivation, heat shock, and viral infection. An eIF-2 associated glycoprotein (p67) has been isolated from rabbit reticulocyte lysates (15). The glycoprotein (p67) promotes protein synthesis in the presence of active eIF-2 kinase by protecting the eIF-2 α-subunit from eIF-2 kinase-catalyzed phosphorylation.

This invention relates to cloning of a nucleotide sequence which encodes a protein that palys an essential role in the removal of the initiator methionine and in the regulation of protein synthesis in eukaryotes.

SUMMARY OF THE INVENTION

An object of the instant invention is providing a nucleotide sequence (SEQ. ID. 1) which encodes for a protein having amino acid sequence substantially similar to eukaryotic initiation factor-2 (eIF-2) associated glycoprotein (p67) and the encoded protein is also capable of removing N-terminal methionine from proteins. The encoded protein having amino acid sequence which is 95% similar to rat initiation factor associated glycoprotein (p67). The protein encoded by the nucleotide sequence may facilitate the function of an eukaryotic initiation factor and thus plays a regulatory role in regulation of protein synthesis. The encoded protein also acts as methionine aminopeptidase that removes the $NH_2$-methionine during protein synthesis. The removal of N-terminal methionine is essential for subsequent modification of proteins, such as N-myristolylation, which is essential for regulation of signal transduction, protein targeting and cancer cell growth in animal system. Therefore, examining the expression of the protein molecule encoded by the nucleotide sequence or the corresponding RNA will provide important information about protein synthesis and other cellular functions. Thus the nucleotide sequence may also be used for monitoring synthesis of methionine aminopeptidase and/or eIF-2 associated glycoprotein (p67).

Yet another object of the instant invention is a method of facilitating protein synthesis in protein expression and/or synthesizing systems. Said nucleotide sequence may be provided to protein synthesizing system to facilitate synthesis of a desired protein by overexpressing the protein encoded by said nucleotide sequence. The encoded protein may facilitate protein synthesis by protecting the eIF-2 from phosphorylation and may also remove N-terminal methionine from the desired protein. The protein synthesizing system may be in-vitro, in-vivo, recombinant or any other system that may become available in future. This discovery also establishes that methionine aminopeptidase and eIF-2 associated glycoprotein (p67) are substantially one and the same protein and thus providing cellular system with the cloned nucleotide sequence will serve both cellular functions.

BRIEF DESCRIPTION OF THE DRAWINGS

FIG. 1. Nucleotide (SEQ ID NO:1), coding region in all upper case letters (SEQ ID NO:2) and deduced amino acid sequence (SEQ ID NO:3) of human methionine aminopeptidase cDNA. The nucleotides are numbered from 5' to 3' on the left margin. The amino acids are numbered at the right margin.

FIG. 2. Alignment of the protein sequences of rat p67 and human methionine aminopeptidase.

DESCRIPTION OF THE INVENTION

Figure 3:
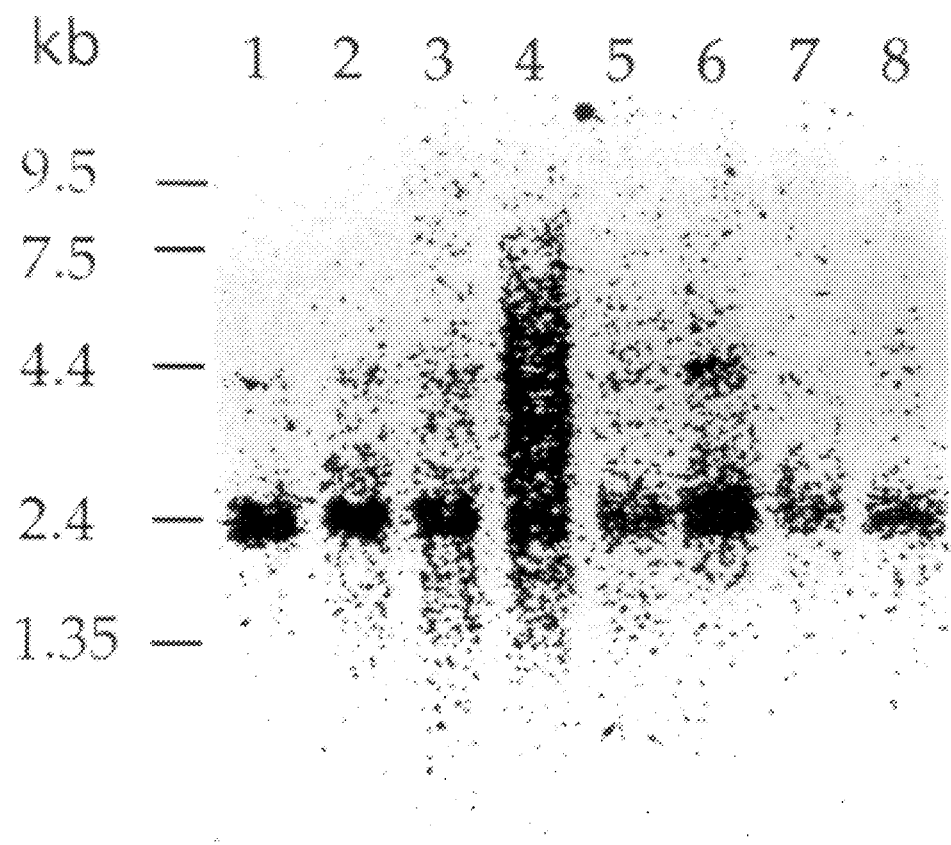
FIG. 3. Hybridization of human multiple tissue northern blot from Clontech (Palo Alto, Calif. USA) with the human methionine aminopeptidase cDNA probe. Each lane contains approximately 2 µg of pure polyA+RNA isolated from the following human tissues: Lane 1: Heart. Lane 2: Brain. Lane 3: Placenta. Lane 4: Lung. Lane 5: Liver. Lane 6: Skeletal muscle. Lane 7: Kidney. Lane 8: Pancrease. After a high stringency wash (0.2×SSC at 60° C.), the blot was analyzed by a phosphoimager.

The nucleotide of the instant invention was cloned from human liver tissue. cDNA of yeast methionine aminopeptidase-2 was used as the hybridization probe. The positive plaques were further purified using the sequence information from the rat p67 gene (16). The p67 gene sequence was amplified in a region where it shows homology with the yeast methionine aminopeptidase-2 gene. An approximately 480 bp was amplified. The plaques producing 480 bp PCR products were the positive clones. The cloned nucleotide sequence encoded a protein which has 95% amino acid sequence similarity with the rat eIF-2 associated glycoprotein p67 and also catalyzed the removal of $NH_2$- methionine from protein. Based on the exceptionally high sequence similarity (95%) of the encoded protein with the p67 protein as well as its methionine amino peptidase activity it is concluded that the encoded protein have at least two cellular functions, the encoded protein may facilitate protein synthesis by protecting the eIF-2 from phosphorylation and may also removed N-terminal methionine from proteins and prepare the proteins for critical cellular functions. In a protein expression system, the introduction of the cloned nucleotide sequence will facilitate protein synthesis.

The invention is further explained with reference to the following example.

EXAMPLE

To clone the nucleotide sequence, the cDNA of yeast methionine aminopeptidase-2 (12) was used as the hybridization probe and screened a human liver Uni-ZAP cDNA library, purchased from Stratagene (La Jolla, Calif. USA). Fifteen positives were obtained from ~1×10$^6$ plaques. For plaque purifications, polymerase chain reaction approach was employed, using two oligonucleotide primers, 5'-GCCATTCAAGAAGTTATGGAGTCCTATGAAG TGGA-3' (forward) (SEQ ID NO:4) and 5'-TAG GTATGTTCAAACTGTGCTGTGTATGATCC-3' (backward), (SEQ ID NO:5) based on the sequence of the rat p67 gene (16) that is conserved between the rat p67 and yeast methionine aminopeptidase 2. Only one PCR product with the expected size of ~480 bp was amplified from some of the positive plaques. Those plaques that produced the 480 bp PCR products were considered to be real positives and further analyzed. The phage DNA from each positive was converted to phagmid vector according to the manufacturer's protocol (Stratagene, La Jolla, Calif. USA). The insert size of the plasmid from each clone was analyzed after Xho I/EcoRI digestion. One clone with the longest insert (~2.0 kb) was used for sequencing. Two sets of nested deletions were generated by using Promega's Erase-a-base kit (Promega, Madison, Mich. USA) from both directions and were sequenced by the dideoxy method using the Sequenase kit from U.S. Biochemical Corp. As shown in FIG. 1, the cloned cDNA insert of 1927 nucleotides contains a single open reading from initiating with an ATG codon at nucleotide position 35–37 and terminating with a TAA stop codon at position 1469–1471. The sequence surrounding the initiating ATG codon, AACATGG, fits well with the consensus established by Kozak (13). In the 3'-untranslated region, there is a putative polyadenylation signal sequence, AATAAA, located 16 nucleotides upstream of the poly(A) tract. The open reading frame encodes a protein 478 amino acids with pI of 5.64 and a calculated molecular mass of 52,891. Amino acid sequence comparison revealed that the sequence of human proteins shares 92% identity and 95% similarity with that of rat p67, and 52% identity with that of yeast methionine aminopeptidase-2. It is worth noting that the amino acid sequence is highly conserved between human methionine aminopeptidase and rat p67 until residue 464, and the discontinuity in homology is caused by a single insertion in the human gene (or a single deletion in the rat gene) with unknown reasons.

The conservation between human methionine aminopeptidase and rat p67 is shown in FIG. 2. The 92% identity mentioned above is reflected in the identical amino acids in human methionine aminopeptidase and rat p67 as shown by vertical bars. The 95% similarity is reflected in the total of identical amino acids and similar or conserved amino acids as identified by vertical bars for identical amino acids and single or double dots for conserved amino acids. Such conserved amino acids substitutions as shown an FIG. 2 are as follows: alanine-valine, serine-alanine, phenylalanine-serine, glycine-serine, threonine-alanine, alanine-proline, glutamine-glutamic acid, lysine-arginine, glutamic acid-aspartic acid, arginine-lysine, isoleucine-threonine, proline-glutamine, proline-threonine, valine-cysteine, lysine-glutamic acid, leucine-valine, and glutamic acid-glycine.

The human methionine aminopeptidase, like yeast methionine aminopeptidase 2 and rat 67, contains highly charged amino acids at the N-terminal region. Human eIF-2 β and yeast protein Sui3 also contain similar polylysine blocks which have been postulated to be involved in protein/protein or protein/nucleic acid interactions. Furthermore, it was found that the human protein shares significant 22% identity with yeast methionine aminopeptidase 1 and the bacterial methionine aminopeptidases (MAPs). Recently, Bazan, J. F. et al. reported that the rat p67 may share a similar folding with bacterial MAP, aminopeptidase-P, prolidases and creatinases (14). They also found that the five residues involved in metal binding, identified by Roderick and Matthews (10), are strictly conserved in all four methionine aminopeptidases, in three aminopeptidase-P, in three prolidases and in rat p67 with only one exception that the site 235 in *E. coli* MAP and in other related enzymes in Glu, whereas its corresponding residue in rat p67 s His. They predicted that p67 may be a metalloprotease which can modify and inactivate the attacking eIF-2 kinases (14). This hypothesis differs from the observations of Gupta and coworkers who showed that the eIF-2 kinase was still active in the presence of rat p67 under their assaying conditions (15, 16). This finding that the human and the rat proteins are homologous to the second methionine aminopeptidase (MAP2) from *S. cerevisia* suggests that p67 is very likely to be a bifunctional protein. To evaluate the tissue distribution and the size of the mRNA of p67, a northern blot analysis was carried out using $^{32}$P-labeled cDNA of human methionine aminopeptidase 2 to probe a RNA blot from Clontech (Palo Alto, Calif. USA). FIG. 3 indicates that the gene of human methionine aminopeptidase 2 is expressed in all tested human tissues, and the size of the corresponding polyA-RNA (~2.1 kb) is close to the size of our cloned cDNA. The extremely high identity between the human methionine aminopeptidase 2 and rat p67 sequences suggests that the function of this protein is fundamentally important and highly conserved.

To determine whether this human protein is indeed a methionine aminopeptidase, this human cloned gene was expressed in insect cells using the baculovirus expression system. The recombinant human protein was purified to homogeneity and used for enzyme assay. It was found that this human protein indeed has methionine aminopeptidase activity, indicating that this human protein has dual functions, i.e. a methionine aminopeptidase-like function in amino-terminal processing and a p67-like function in regulation of protein synthesis.

REFERENCE

All references cited herein are incorporated herein by reference in entirety.
1. Ball L. A., Kaesberg P. (1973) *J. Mol. Biol.* 79:531–537
2. Moerschell R. P., Hosokawa Y., Tsunasawa S., Sherman F. (1990) *J. Biol. Chem* 265:19638–19643

3. Ben-Bassat A., Bauer K., Chang S. Y., Myambo K., Boosman A., Chang S. (1987) *J. Bacteriol.* 169:751–757
4. Huang S., Elliott R. C., Liu P. S., Koduri R. K., Weickmann J. L., Lee J. H., Blair L. C., Ghosh-Dastidar P., Bradshaw R. A., Bryan K. M., et al (1987) *Biochemistry* 26:8242–8246
5. Miller C. G., Strauch K. L., Kukral A. M., Miller J. L., Wingfield P. T., Mazzei G. J., Werlen R. C., Graber P., Movva N. R. (1987) *Proc. Natl. Acad Sci USA* 84:2718–2722
6. Gordon J. I., Duronio R. J., Rudnick D. A., Adams S. P., Gokel G. W. (1991) *J. Biol. Chem.* 266:8647–8650
7. Duronio R. J., Towler D. A., Heuckeroth R. O., Gordon J. I. (1989) *Science* 243:796–800
8. Chang Y. H., Teichert U., Smith J. A. (1990) *J. Biol. Chem.* 265:19892–19897
9. Kendall R. L., Bradshaw R. A. (1992) *J. Biol. Chem.* 267:20667–20673
10. Roderick S. L., Matthews B. W. (1993) *Biochemistry* 32:3907–3912
11. Chang Y. H., Teichet U., Smith J. A. (1992) *J. Biol. Chem.* 267–8007–11
12. Li X., Chang Y. H. (1995) *Proc. Natl. Acad Sci* 92:12375–12361
13. Kozak M. (1991) *J. Biol. Chem.* 26:19867–19870
14. Bazan J. F., Weaver L. H., Roderick S., Huber R. and Mathew B. W. (1994) *Proc. Natl. Acad Sci USA* 91:2473–2477
15. Ray M. K., Chakarabort A., Datta B., Chattopadhyay A., Saha D., Bose A., Kinzy T. G., Wu S., Hileman R. E., Merrick W. C. and Gupta N. K. (1993) *Biochemistry* 32:5151–5159
16. Wu S., Gupta S., Chatterjee N., Hileman R. E., Kinzy T. G., Denslow N. D., Merrick W. C., Chakarabarti D., Osterman J. C. and Gupta N. K. (1993) *J. Biol. Chem.* 268:10796–10801

---

What I claim my invention is:

1. An isolated polynucleotide or a polynucleotide complementary thereto, wherein said polynucleotide comprises a nucleotide sequence encoding a methionine aminopeptidase, and wherein said polynucleotide complementary thereto hybridizes under high stringency conditions to SEQ ID NO:1 or SEQ ID NO:2.

2. The isolated polynucleotide or polynucleotide complementary thereto according to claim 1 wherein the methionine aminopeptidase comprises a sequence as set forth in SEQ ID NO:3.

3. The isolated polynucleotide or polynucleotide complementary thereto according to claim 2 comprising SEQ ID NO:1.

4. The isolated polynucleotide or polynucleotide complementary thereto according to claim 2 comprising SEQ ID NO:2.

5. A vector comprising a polynucleotide as defined in claim 1.

6. A recombinant host cell comprising the poly nucleotide of claim 1.

7. The host cell of claim 6 wherein said host cell is a baculovirus expression system.

8. An isolated nucleic acid comprising a nucleotide sequence encoding a methionine aminopeptidase which is a conservatively substituted variant of SEQ ID NO:3.

9. The isolated polynucleotide or polynucleotide complementary thereto according to claim 2 consisting of a sequence which encodes the protein of SEQ ID NO:3.

10. The isolated polynucleotide or polynucleotide complementary thereto according to claim 3 consisting of SEQ ID NO:1.

11. The isolated polynucleotide or polynucleotide complementary thereto according to claim 4 consisting of SEQ ID NO:2.

12. An isolated nucleic acid which encodes an enzymatically active fragment of the protein described in SEQ ID NO:3.

13. An isolated nucleic acid comprising a polynucleotide of at least 480 contiguous nucleotides or a polynucleotide complimentary thereto, wherein said polynucleotide hybridizes under high stringency conditions to SEQ ID NO:1 or SEQ ID NO:2.

14. The isolated nucleic acid to claim 13 wherein the polynucleotide hybridizes under high stringency conditions to an mRNA, and wherein said mRNA encodes a human methionine aminopeptidase.

15. A recombinant DNA method for expressing a methionine aminopeptidase comprising:

(a) cloning a gene comprising the polynucleotide or polynucleotide complimentary thereto of claim 1, into a host cell expression system; and (b) expressing the cloned gene.

16. The recombinant DNA method of claim 15 wherein said host cell expression system is a baculovirus expression system.

* * * * *

UNITED STATES PATENT AND TRADEMARK OFFICE
CERTIFICATE OF CORRECTION

PATENT NO. : 5,885,820
DATED : March 23, 1999
INVENTOR(S) : Yie-Hwa Chang

It is certified that error appears in the above-indentified patent and that said Letters Patent is hereby corrected as shown below:

Column 12, line 60, delete "poly nucleotide" and substitute therefor --polynucleotide--.

Column 13, line 15, delete "complimentary" and substitute therefor --complementary--.

Column 14, line 1, after the word "acid" add --according--.

Column 14, line 9, delete "complimentary" and substitute therefor --complementary--.

Signed and Sealed this

Twenty-second Day of May, 2001

Attest:

NICHOLAS P. GODICI

*Attesting Officer*   *Acting Director of the United States Patent and Trademark Office*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 1927 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
CTCTGTCTCA  TTCCCTCGCG  CTCTCTCGGG  CAACATGGCG  GGTGTGGAGG  AGGTAGCGGC    60
CTCCGGGAGC  CACCTGAATG  GCGACCTGGA  TCCAGACGAC  AGGGAAGAAG  GAGCTGCCTC   120
TACGGCTGAG  GAAGCAGCCA  AGAAAAAAAG  ACGAAAGAAG  AAGAAGAGCA  AAGGGCCTTC   180
TGCAGCAGGG  GAACAGGAAC  CTGATAAAGA  ATCAGGAGCC  TCAGTGGATG  AAGTAGCAAG   240
ACAGTTGGAA  AGATCAGCAT  TGGAAGATAA  AGAAAGAGAT  GAAGATGATG  AAGATGGAGA   300
TGGCGATGGA  GATGGAGCAA  CTGGAAAGAA  GAAGAAAAG   AAGAAGAAGA  AGAGAGGACC   360
AAAAGTTCAA  ACAGACCCTC  CCTCAGTTCC  AATATGTGAC  CTGTATCCTA  ATGGTGTATT   420
TCCCAAAGGA  CAAGAATGCG  AATACCCACC  CACACAAGAT  GGGCGAACAG  CTGCTTGGAG   480
AACTACAAGT  GAAGAAAAGA  AAGCATTAGA  TCAGGCAAGT  GAAGAGATTT  GGAATGATTT   540
TCGAGAAGCT  GCAGAAGCAC  ATCGACAAGT  TAGAAAATAC  GTAATGAGCT  GGATCAAGCC   600
TGGGATGACA  ATGATAGAAA  TCTGTGAAAA  GTTGGAAGAC  TGTTCACGCA  AGTTAATAAA   660
AGAGAATGGA  TTAAATGCAG  GCCTGGCATT  TCCTACTGGA  TGTTCTCTCA  ATAATTGTGC   720
TGCCCATTAT  ACTCCCAATG  CCGGTGACAC  AACAGTATTA  CAGTATGATG  ACATCTGTAA   780
AATAGACTTT  GGAACACATA  TAAGTGGTAG  GATTATTGAC  TGTGCTTTTA  CTGTCACTTT   840
TAATCCCAAA  TATGATACGT  TATTAAAAGC  TGTAAAAGAT  GCTACTAACA  CTGGAATAAA   900
GTGTGCTGGA  ATTGATGTTC  GTCTGTGTGA  TGTTGGTGAG  GCCATCCAAG  AAGTTATGGA   960
GTCCTATGAA  GTTGAAATAG  ATGGGAAGAC  ATATCAAGTG  AAACCAATCC  GTAATCTAAA  1020
TGGACATTCA  ATTGGGCAAT  ATAGAATACA  TGCTGGAAAA  ACAGTGCCGA  TTGTGAAAGG  1080
AGGGGAGGCA  ACAAGAATGG  AGGAAGGAGA  AGTATATGCA  ATTGAAACCT  TTGGTAGTAC  1140
```

-continued

| | | | | | |
|---|---|---|---|---|---|
|AGGAAAAGGT|GTTGTTCATG|ATGATATGGA|ATGTTCACAT|TACATGAAAA|ATTTTGATGT 1200|
|TGGACATGTG|CCAATAAGGC|TTCCAAGAAC|AAAACACTTG|TTAAATGTCA|TCAATGAAAA 1260|
|CTTTGGAACC|CTTGCCTTCT|GCCGCAGATG|GCTGGATCGC|TTGGGAGAAA|GTAAATACTT 1320|
|GATGGCTCTG|AAGAATCTGT|GTGACTTGGG|CATTGTAGAT|CCATATCCAC|CATTATGTGA 1380|
|CATTAAAGGA|TCATATACAG|CGCAATTTGA|ACATACCATC|CTGTTGCGTC|AACATGTAA 1440|
|AGAAGTTGTC|AGCAGAGGAG|ATGACTATTA|AACTTAGTCC|AAAGCCACCT|CAACACCTTT 1500|
|ATTTTCTGAG|CTTTGTTGGA|AAACATGATA|CCAGAATTAA|TTTGCCACAT|GTTGTCTGTT 1560|
|TTAACAGTGG|ACCCATGTAA|TACTTTTATC|CATGTTTAAA|AAGAAGGAAT|TTGGACAAAG 1620|
|GCAAACCGTC|TAATGTAATT|AACCAACGAA|AAAGCTTTCC|GGACTTTTAA|ATGCTAACTG 1680|
|TTTTTCCCCT|TCCTGTCTAG|GAAAATGCTA|TAAAGCTCAA|ATTAGTTAGG|AATGACTTAT 1740|
|ACGTTTTGTT|TTGAATACCT|AAGAGATACT|TTTTGGATAT|TTATATTGCC|ATATTCTTAC 1800|
|TTGAATGCTT|TGAATGACTA|CATCCAGTTC|TGCACCTATA|CCCTCTGGTG|TTGCTTTTA 1860|
|ACCTTCCTGG|AATCCATTTC|TAAAAAATAA|AGACATTTTC|AGATCTGAAA|AAAAAAAAA 1920|
|AAAAAAA| | | | |1927|

( 2 ) INFORMATION FOR SEQ ID NO:2:

( i ) SEQUENCE CHARACTERISTICS:
        ( A ) LENGTH: 1434 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
|ATGGCGGGTG|TGGAGGAGGT|AGCGGCCTCC|GGGAGCCACC|TGAATGGCGA|CCTGGATCCA 60|
|GACGACAGGG|AAGAAGGAGC|TGCCTCTACG|GCTGAGGAAG|CAGCCAAGAA|AAAAAGACGA 120|
|AAGAAGAAGA|AGAGCAAAGG|GCCTTCTGCA|GCAGGGGAAC|AGGAACCTGA|TAAAGAATCA 180|
|GGAGCCTCAG|TGGATGAAGT|AGCAAGACAG|TTGGAAAGAT|CAGCATTGGA|AGATAAAGAA 240|
|AGAGATGAAG|ATGATGAAGA|TGGAGATGGC|GATGGAGATG|GAGCAACTGG|AAAGAAGAAG 300|
|AAAAGAAGA|AGAAGAAGAG|AGGACCAAAA|GTTCAAACAG|ACCCTCCCTC|AGTTCCAATA 360|
|TGTGACCTGT|ATCCTAATGG|TGTATTTCCC|AAAGGACAAG|AATGCGAATA|CCCACCCACA 420|
|CAAGATGGGC|GAACAGCTGC|TTGGAGAACT|ACAAGTGAAG|AAAAGAAAGC|ATTAGATCAG 480|
|GCAAGTGAAG|AGATTTGGAA|TGATTTTCGA|GAAGCTGCAG|AAGCACATCG|ACAAGTTAGA 540|
|AAATACGTAA|TGAGCTGGAT|CAAGCCTGGG|ATGACAATGA|TAGAAATCTG|TGAAAAGTTG 600|
|GAAGACTGTT|CACGCAAGTT|AATAAAGAG|AATGGATTAA|ATGCAGGCCT|GGCATTTCCT 660|
|ACTGGATGTT|CTCTCAATAA|TTGTGCTGCC|CATTATACTC|CCAATGCCGG|TGACACAACA 720|
|GTATTACAGT|ATGATGACAT|CTGTAAAATA|GACTTTGGAA|CACATATAAG|TGGTAGGATT 780|
|ATTGACTGTG|CTTTTACTGT|CACTTTTAAT|CCCAAATATG|ATACGTTATT|AAAAGCTGTA 840|
|AAAGATGCTA|CTAACACTGG|AATAAAGTGT|GCTGGAATTG|ATGTTCGTCT|GTGTGATGTT 900|
|GGTGAGGCCA|TCCAAGAAGT|TATGGAGTCC|TATGAAGTTG|AAATAGATGG|GAAGACATAT 960|
|CAAGTGAAAC|CAATCCGTAA|TCTAAATGGA|CATTCAATTG|GGCAATATAG|AATACATGCT 1020|
|GGAAAAACAG|TGCCGATTGT|GAAAGGAGGG|GAGGCAACAA|GAATGGAGGA|AGGAGAAGTA 1080|
|TATGCAATTG|AAACCTTTGG|TAGTACAGGA|AAAGGTGTTG|TTCATGATGA|TATGGAATGT 1140|

-continued

```
TCACATTACA  TGAAAAATTT  TGATGTTGGA  CATGTGCCAA  TAAGGCTTCC  AAGAACAAAA      1200

CACTTGTTAA  ATGTCATCAA  TGAAAACTTT  GGAACCCTTG  CCTTCTGCCG  CAGATGGCTG      1260

GATCGCTTGG  GAGAAAGTAA  ATACTTGATG  GCTCTGAAGA  ATCTGTGTGA  CTTGGGCATT      1320

GTAGATCCAT  ATCCACCATT  ATGTGACATT  AAAGGATCAT  ATACAGCGCA  ATTTGAACAT      1380

ACCATCCTGT  TGCGTCCAAC  ATGTAAAGAA  GTTGTCAGCA  GAGGAGATGA  CTAT            1434
```

( 2 ) INFORMATION FOR SEQ ID NO:3:

( i ) SEQUENCE CHARACTERISTICS:
        ( A ) LENGTH: 478 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:3:

```
Met  Ala  Gly  Val  Glu  Glu  Val  Ala  Ala  Ser  Gly  Ser  His  Leu  Asn  Gly
 1              5                        10                       15

Asp  Leu  Asp  Pro  Asp  Asp  Arg  Glu  Glu  Gly  Ala  Ala  Ser  Thr  Ala  Glu
               20                       25                       30

Glu  Ala  Ala  Lys  Lys  Lys  Arg  Arg  Lys  Lys  Lys  Lys  Ser  Lys  Gly  Pro
          35                       40                       45

Ser  Ala  Ala  Gly  Glu  Gln  Glu  Pro  Asp  Lys  Glu  Ser  Gly  Ala  Ser  Val
     50                       55                       60

Asp  Glu  Val  Ala  Arg  Gln  Leu  Glu  Arg  Ser  Ala  Leu  Glu  Asp  Lys  Glu
65                       70                       75                       80

Arg  Asp  Glu  Asp  Asp  Glu  Asp  Gly  Asp  Gly  Asp  Gly  Asp  Gly  Ala  Thr
                         85                       90                       95

Gly  Lys  Lys  Lys  Lys  Lys  Lys  Lys  Lys  Arg  Gly  Pro  Lys  Val  Gln
                    100                      105                      110

Thr  Asp  Pro  Pro  Ser  Val  Pro  Ile  Cys  Asp  Leu  Tyr  Pro  Asn  Gly  Val
               115                      120                      125

Phe  Pro  Lys  Gly  Gln  Glu  Cys  Glu  Tyr  Pro  Pro  Thr  Gln  Asp  Gly  Arg
          130                      135                      140

Thr  Ala  Ala  Trp  Arg  Thr  Thr  Ser  Glu  Glu  Lys  Lys  Ala  Leu  Asp  Gln
145                      150                      155                      160

Ala  Ser  Glu  Glu  Ile  Trp  Asn  Asp  Phe  Arg  Glu  Ala  Ala  Glu  Ala  His
                    165                      170                      175

Arg  Gln  Val  Arg  Lys  Tyr  Val  Met  Ser  Trp  Ile  Lys  Pro  Gly  Met  Thr
               180                      185                      190

Met  Ile  Glu  Ile  Cys  Glu  Lys  Leu  Glu  Asp  Cys  Ser  Arg  Lys  Leu  Ile
          195                      200                      205

Lys  Glu  Asn  Gly  Leu  Asn  Ala  Gly  Leu  Ala  Phe  Pro  Thr  Gly  Cys  Ser
     210                      215                      220

Leu  Asn  Asn  Cys  Ala  Ala  His  Tyr  Thr  Pro  Asn  Ala  Gly  Asp  Thr  Thr
225                      230                      235                      240

Val  Leu  Gln  Tyr  Asp  Asp  Ile  Cys  Lys  Ile  Asp  Phe  Gly  Thr  His  Ile
                    245                      250                      255

Ser  Gly  Arg  Ile  Ile  Asp  Cys  Ala  Phe  Thr  Val  Thr  Phe  Asn  Pro  Lys
               260                      265                      270

Tyr  Asp  Thr  Leu  Leu  Lys  Ala  Val  Lys  Asp  Ala  Thr  Asn  Thr  Gly  Ile
          275                      280                      285

Lys  Val  Ala  Gly  Ile  Asp  Val  Arg  Leu  Cys  Asp  Val  Gly  Glu  Ala  Ile
     290                      295                      300
```

```
Gln  Glu  Val  Met  Glu  Ser  Tyr  Glu  Val  Glu  Ile  Asp  Gly  Lys  Thr  Tyr
305                      310                      315                      320

Gln  Val  Lys  Pro  Ile  Arg  Asn  Leu  Asn  Gly  His  Ser  Ile  Gly  Gln  Tyr
                    325                      330                      335

Arg  Ile  His  Ala  Gly  Lys  Thr  Val  Pro  Ile  Val  Lys  Gly  Gly  Glu  Ala
               340                      345                      350

Thr  Arg  Met  Glu  Glu  Gly  Glu  Val  Tyr  Ala  Ile  Glu  Thr  Phe  Gly  Ser
          355                      360                      365

Thr  Gly  Lys  Gly  Val  Val  His  Asp  Asp  Met  Glu  Cys  Ser  His  Tyr  Met
     370                      375                      380

Lys  Asn  Phe  Asp  Val  Gly  His  Val  Pro  Ile  Arg  Leu  Pro  Arg  Thr  Lys
385                      390                      395                      400

His  Leu  Leu  Asn  Val  Ile  Asn  Glu  Asn  Phe  Gly  Thr  Leu  Ala  Phe  Cys
                405                      410                      415

Arg  Arg  Trp  Leu  Asp  Arg  Leu  Gly  Glu  Ser  Lys  Tyr  Leu  Met  Ala  Leu
               420                      425                      430

Lys  Asn  Leu  Cys  Asp  Leu  Gly  Ile  Val  Asp  Pro  Tyr  Pro  Pro  Leu  Cys
          435                      440                      445

Asp  Ile  Lys  Gly  Ser  Tyr  Thr  Ala  Gln  Phe  Glu  His  Thr  Ile  Leu  Leu
     450                      455                      460

Arg  Pro  Thr  Cys  Lys  Glu  Val  Val  Ser  Arg  Gly  Asp  Asp  Tyr
465                      470                      475
```

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCCATTCAAG AAGTTATGGA GTCCTATGAA GTGGA      35

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TAGGTATGTT CAAACTGTGC TGTGTATGAT CC      32